US007888033B2

(12) United States Patent
Hoon et al.

(10) Patent No.: US 7,888,033 B2
(45) Date of Patent: Feb. 15, 2011

(54) USE OF ID4 FOR DIAGNOSIS AND TREATMENT OF CANCER

(75) Inventors: Dave S. B. Hoon, Los Angeles, CA (US); Naoyuki Umetani, Tokyo (JP)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 12/417,577

(22) Filed: Apr. 2, 2009

(65) Prior Publication Data
US 2009/0263812 A1 Oct. 22, 2009

Related U.S. Application Data

(63) Continuation-in-part of application No. 11/345,836, filed on Feb. 1, 2006, now Pat. No. 7,588,894.

(60) Provisional application No. 60/649,650, filed on Feb. 1, 2005.

(51) Int. Cl.
*C12Q 1/68* (2006.01)
*C07H 21/02* (2006.01)
*C07H 21/04* (2006.01)

(52) U.S. Cl. ............................ 435/6; 536/23.1; 536/24.3

(58) Field of Classification Search .................. 435/6, 435/91.2; 536/23.1, 24.3
See application file for complete search history.

(56) References Cited

U.S. PATENT DOCUMENTS

| 7,588,894 B2 * | 9/2009 | Hoon et al. ..................... 435/6 |
| 2007/0020646 A1 | 1/2007 | Hoon et al. |
| 2009/0263812 A1 * | 10/2009 | Hoon et al. ..................... 435/6 |

FOREIGN PATENT DOCUMENTS

| WO | WO2004/074510 | * | 9/2004 |
| WO | 2006/084051 A2 | | 8/2006 |

OTHER PUBLICATIONS

Rigolet et al. cDNA cloning, tissue distribution and chromosomal localization of the human ID4 gene. DNA Research 5(5) : 309-313 (1998).*
Rebhan, M., Chalifa-Caspi, V., Prilusky, J., Lancet, D.: GeneCards: encyclopedia for genes, proteins and diseases. Weizmann Institute of Science, Bioinformatics Unit and Genome Center (Rehovot, Israel), 1997. GeneCard for [ID4] [Mar. 22, 2007]).*
Fong et al., Id genes and proteins as promising targets in cancer therapy. Trends in Molecular Medicine 10(8) : 387-392 (2004).*
Das et al., DNA Methylation and Cancer. J. of Clinical Oncology 22(22) :4632-4642 (2004).*
Perk et al.,. ID Family of Helix-Loop-Helix proteins in cancer. Nature Reviews Cancer 5: 603-614 (2005).*
Umetani et al., Epigenetic inactivation of ID4 in colorectal carcinomas correlates with poor differentiation and unfavorable prognosis. Clinical Cancer Research 10 : 7475-7483 (2004).*
Chan et al., Downregulation of ID4 by promoter hypermethylation in gastric adenocarcinoma. Oncogene 22 : 6946-6953 (2003).*
Umetani et al., Aberrant hypermethylation of ID4 gene promoter region increases risk of lymph node metastasis in T1 breast cancer. Oncogene 24:4721-4727, 2005.*
Carey et al., Inhibitor of differentiation 4 (Id4) is a potential tumor suppressor in prostate cancer. BMC Cancer. 9:173 (15 pages) (2009).*
Kloeppel et al., DE 2004-102004042822 (Aug. 2004) abstract only.*
Yu et al., Global assessment of promoter methylation in a mouse model of cancer identifies ID4 as a putative tumor-suppressor gene in human leukemia. Nature Genetics 37 (3) :265-274 (Feb. 20, 2005).*
Richemann et al., "Mutually Exclusive Expression of Two Dominant-Negative Helix-Loop-Helix (dnHLH) Genes, *Id4* and *Id3* in the Developing Brain of the Mouse Suggests Distinct Regulatory Roles of these dnHLH Proteins During Cellular Proliferation and Differentiation of the Nervous System," *Cell Growth & Differentiation*, (1995), vol. 6, pp. 837-843.
Welcsh et al., "BRCA1 Transcriptionally Regulates Genes Involved in Breast Tumorigenesis," *Proc. Natl. Acad. Sci. USA*, (2002), vol. 99, pp. 7560-7565.
Beger et al., "Identification of *Id4* as a Regulator of *BRCA1* Expression by Using a Ribozyme-Library-Based Inverse Genomics Approach," *Proc. Natl. Acad. Sci. USA*, (2001), vol. 98, pp. 130-135.
Shan et al., "*Id4* Regulates Mammary Epithelial Cell Growth and Differentiation and is Overexpressed in Rat Mammary Gland Carcinomas," *Am. J. Pathol* ., (2003), vol. 163, pp. 2495-2502.
Umetani et al., "Allelic Imbalance of *APAP-1* Locus at *12q23* is Related to Progression of Colorectal Carcinoma," *Oncogene* (2004), vol. 23, pp. 8292-8300.
Pagliuca et al., "Molecular cloning of *ID4*, a Novel Dominant Negative Helix-Loop-Helix Human Gene on Chromosome *6p21.3-p22*," *Genomics*, (1995), vol. 27, pp. 200-203.
United States Patent and Trademark Office, International Search Report and Written Opinion for PCT/US2010/029814, dated Jul. 2, 2010.
Verheul, HMW et al, "Are tumours angiogenesis-dependent?" Journal of Pathology, 2004, 202:5-13 (Published online Oct. 13, 2003).

* cited by examiner

*Primary Examiner*—Ethan Whisenant
(74) *Attorney, Agent, or Firm*—Perkins Coie LLP

(57) ABSTRACT

The invention relates to a method of determining whether a human subject is suffering from or at risk for developing pancreatic cancer by determining the methylation level of an ID4 gene promoter or the expression level of an ID4 gene in a biological sample from a human subject. Also disclosed are a method of analyzing the methylation level of an ID4 gene promoter or the expression level of an ID4 gene in a pancreatic cancer cell, and a method of inhibiting the methylation of an ID4 gene promoter or enhancing the expression of an ID4 gene by contacting a pancreatic cancer cell with a compound that decreases the methylation level of an ID4 gene promoter or increases the expression level of an ID4 gene in the cell.

20 Claims, 4 Drawing Sheets

SEQUENCE LISTING

<160> NUMBER OF SEQ ID NOS: 1

<210> SEQ ID NO 1
<211> LENGTH: 1500
<212> TYPE: DNA
<213> ORGANISM: Homo sapiens
<220> FEATURE:
<221> NAME/KEY: misc_feature
<222> LOCATION: (1001)..(1001)
<223> OTHER INFORMATION: Transcriptional start site

<400> SEQUENCE: 1

```
cattaatggc ctaaattaag ttacaggtat gaattttaca taaaacagat taatattata      60
tgtcataatg gaattttaaa tattccgtgt ccatgcattt ttaatcttta cgtgctctaa     120
ttgaatgcgc aaggcaactg catttcttga gcccactttt gcatttagat ggggtaaaag     180
aaccccccc acgttttgt tttatttata ttcccttcac caaaaacctg cattcgattc       240
ggcattcttt tccttctttt tttttctact tttgctaagc tttagcattt tttaaaaga      300
aaacggaaag gctacacatt ccattccatc attatggttt cggcaaatgt gaaaaggcga     360
ataatgaaac ggaggaggga aatatagaac agaatgaacg tgccttcttg aacagcgcgt     420
ctttcttaag gcactggaat cccacggatg gagtgatggg tggcggaggg tccctgggcg     480
ccgtgctatt aggagtggca gggtatccgc gagcagggcc caggcgctcc ctcagcagcc     540
tagtcgggat aaggggggcg gtggagagtg aattccggcc gcacattccc gcagttcttc     600
gcaggaactt cgctctctct tttcccctcc cttgggcaca catcagcctg gcccgactcc     660
cactcagctc tcttttctca gaaccccgac ccacagcgtt gacggaatgg agtgcccttc     720
ccattggccc gagcgtcatt ccccgaggtg gcactgcccg cctgattggc tggccactcc     780
agacccccg cccactcctc cactcgggta gccggactcc ccgcccccca gcaccgcccg      840
gagccccgc cctcgcctct ccctccgcgc ccccgcccgc gcgcccagcg ggctccgctc      900
ggctcgcgct gcgacccggc ccgcgcgctg gtcccgcccc cggggcgcac ggctctataa     960
atacagctgc gcggcgggcc gggcgagagc gtagtggagg aggcgcggtt gtgagtagta    1020
ccgggagtgg ggtgatcccg ggctagggga gcgcggcggc cgcgatcggg cttagtcgga   1080
gctccgaagg gagtgactag gacacccggg tgggctactt ttcttccggt gcttttgctt   1140
ttttttcct ttgggctcgg gctgagtgtc gcccactgag caaagattcc ctcgtaaaac    1200
ccagagcgac cctcccgtca attgttgggc tcgggagtgt cgcggtgccc cgagcgcgcc   1260
gggcgcggag gcaaagggag cggagccggc cgcggacggg gcccggagct tgcctgcctc   1320
cctcgctcgc cccagcgggt tcgctcgcgt agagcgcagg gcgcgcgcga tgaaggcggt   1380
gagcccggtg cgcccctcgg gccgcaaggc gccgtcgggc tgcggcggcg gggagctggc   1440
gctgcgctgc ctggccgagc acggccacag cctgggtggc tccgcagccg cggcggcggc   1500
```

US 7,888,033 B2

USE OF ID4 FOR DIAGNOSIS AND TREATMENT OF CANCER

RELATED APPLICATIONS

This application is a continuation-in-part application of U.S. application Ser. No. 11/345,836, filed Feb. 1, 2006, which claims priority to U.S. Provisional Application Ser. No. 60/649,650, filed Feb. 1, 2005. The contents of both U.S. application Ser. No. 11/345,836 and U.S. Provisional Application Ser. No. 60/649,650 are incorporated herein by reference in their entirety.

FIELD OF THE INVENTION

The present invention relates in general to inhibitors of DNA binding proteins. More specifically, the invention relates to the use of ID4 for diagnosis, prognosis, and treatment of pancreatic cancer.

BACKGROUND OF THE INVENTION

Methylation of cytosines in CpG islands in the promoter region affects promoter activity and can down-regulate gene transcription. Because the promoter hypermethylation of genes in cancer cells is as significant as deletions or mutations, hypermethylation of key regulatory genes can play a significant role in transformation and tumor progression. Progression of transformed cells requires regulatory gene inactivation that promotes growth, dedifferentiation, invasion, and/or metastasis.

Transcription factors containing a basic helix-loop-helix (bHLH) motif regulate the expression of certain tissue-specific genes and have important roles in cell differentiation and embryonic developmental processes. DNA-binding activity of the bHLH proteins is dependent on formation of homo- and/or hetero-dimers. ID family proteins, which are distinct members of the helix-loop-helix (HLH) protein family, contain the HLH-dimerization domain but lack the DNA-binding basic domain. Consequently, ID proteins dominantly inhibit binding to DNA and transcriptional transactivation by forming heterodimers with bHLH proteins and modulate various key developmental processes. Currently, four known human ID proteins have been identified. Expression studies have shown that ID proteins play critical roles in early embryonic development. They are also involved in angiogenesis, lymphocyte development, cell cycle control, and cellular senescence. The involvement of ID proteins in neoplastic processes has been suggested. Increased ID1 and ID2 expression has been reported in various tumor types, including adenocarcinomas arising from the colon and pancreas. Transgene expression of ID1 and ID2 in mice has resulted in tumor formation in the intestinal epithelium and lymphoid organs, respectively. Expression of ID3 has been more variable; studies report both up-regulation and down-regulation in different tumor types.

SUMMARY OF THE INVENTION

This invention relates to methods for diagnosis, prognosis, and treatment of pancreatic cancer using ID4.

In one aspect, the invention features a method of determining whether a human subject is suffering from or at risk for developing pancreatic cancer. The method comprises obtaining a biological sample from a human subject, and determining the methylation level of an inhibitor of DNA binding 4 (ID4) gene promoter or the expression level of an ID4 gene in the sample. If the methylation level of the ID4 gene promoter in the sample is higher than a control methylation level or the expression level of the ID4 gene in the sample is lower than a control expression level, it indicates that the human subject is likely to be suffering from or at risk for developing pancreatic cancer.

In another aspect, the invention features a method of analyzing the methylation level of an ID4 gene promoter or the expression level of an ID4 gene. The method comprises providing a pancreatic cancer cell, and determining the methylation level of an ID4 gene promoter or the expression level of an ID4 gene in the cell.

The method may further comprises analyzing the angiogenesis or chemotaxis of the cell. If the methylation level of the ID4 gene promoter in the cell is higher than a control methylation level or the expression level of the ID4 gene in the cell is lower than a control expression level, it indicates an increase in the angiogenesis or chemotaxis of the cell.

The invention also provides a method of inhibiting the methylation of an ID4 gene promoter or enhancing the expression of an ID4 gene in a cell. The method comprises providing a pancreatic cancer cell, and contacting the cell with a compound that decreases the methylation level of an ID4 gene promoter or increases the expression level of an ID4 gene in the cell.

For example, the compound may be a demethylation agent such as 5-aza-cytidine or a histone deacetylase (HDAC) inhibitor such as Trichostatin. Alternatively, the compound may be an ID4 protein, a nucleic acid encoding an ID4 protein, or an agent that activates an ID4 gene.

In the methods described above, the pancreatic cancer may be primary or metastatic. The methylation level of the ID4 gene promoter may be determined by quantitative methylation-specific polymerase chain reaction (MSP) or bisulfite sequencing. The expression level of the ID4 gene may be determined at the mRNA level (e.g., by quantitative polymerase chain reaction (PCR)) or the protein level (e.g., by immunohistochemistry (IHC)).

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

Figure 1:
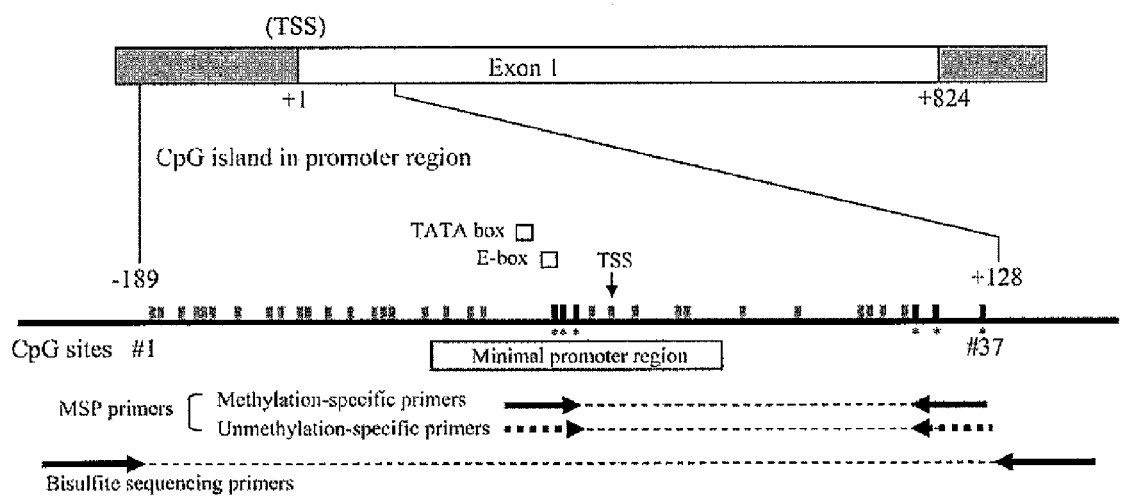
FIG. 1. Structure of the promoter region of ID4 gene and the primer design for methylation-specific PCR and bisulfite sequencing. CpG sites in the annealing site of methylation-specific PCR primers are indicated with "*". (TSS, transcription start site)

The invention is based at least in part upon the unexpected discovery that the expression of transcription factor ID4 results in the inhibition of pancreatic cancer cell chemotaxis and endothelial cell angiogenesis, and ID4 expression is regulated by hypermethylation of the CpG islands in the promoter region of ID4.

Accordingly, the invention provides a method of analyzing the methylation level of an ID4 gene promoter or the expression level of an ID4 gene in a pancreatic cancer cell. The pancreatic cancer cell may be obtained from a cell culture or a biological sample from a subject having pancreatic cancer. It can be either a primary pancreatic cancer cell or a metastatic pancreatic cancer cell. The methylation level of an ID4 gene promoter or the expression level of an ID4 gene in the cell is then determined.

"Subject," as used herein, refers to a human or animal, including all vertebrates, e.g., mammals, such as primates (particularly higher primates), sheep, dog, rodents (e.g., mouse or rat), guinea pig, goat, pig, cat, rabbit, cow; and non-mammals, such as chicken, amphibians, reptiles, etc. In a preferred embodiment, the subject is a human. In another embodiment, the subject is an experimental animal or animal suitable as a disease model.

A biological sample from a subject can be a tissue sample (e.g., a biopsy specimen sample, a normal or benign tissue sample, a freshly prepared tumor sample, a frozen tumor tissue sample, a paraffin-embedded tumor sample, a primary tumor sample, or a metastasis sample) or a body fluid sample (e.g., any body fluid in which cancer cells or acellular DNA may be present, including, without limitation, blood, bone marrow, cerebral spinal fluid, peritoneal fluid, pleural fluid, lymph fluid, ascites, serous fluid, sputum, lacrimal fluid, stool, or urine). These tissues and body fluids can be collected using any of the methods well known in the art.

The ID4 gene is known in the art. For example, the human ID4 gene is reported to be located at Entrez Gene cytogenetic band 6p22-p21, Ensemble cytogenetic band 6p22.3, and HGNC cytogenetic band 6p22.3. The DNA sequence around the human ID4 promoter region is shown below.

[Upstream 1,000 bp]
(SEQ ID NO: 1)
cattaatggcctaaattaagttacaggtatgaattttacataaaacagat taatattatatgtcataatggaattttaaatattccgtgtccatgcattt ttaatctttacgtgctctaattgaatgcgcaaggcaactgcatttcttga gcccacttttgcatttagatggggtaaaagaaccccccccacgttttttgt tttatttatattcccttcaccaaaaacctgcattcgattcggcattcttt tccttcttttttttttctacttttgctaagctttagcatttttttaaaaaga aaacggaaaggctacacattccattccatcattatggtttcggcaaatgt gaaaaggcgaataatgaaacggaggagggaaatatagaacagaatgaacg tgccttcttgaacagcgcgtctttcttaaggcactggaatcccacggatg gagtgatgggtggcggagggtccctgggcgccgtgctattaggagtggca gggtatccgagagcagggcccaggcgctccctcagcagcctagtcgggat aaggggggcggtggagagtgaattccggccgaacattcccgcagttcttc gcaggaacttcgctctctcttttcccctccctgggcacacatcagcctg gcccgactcccactcagctctcttttctcagaaccccgaccacagcgtt gacggaatggagtgcccttcccattggcccgagcgtcattcccgaggtg gcactgcccgcctgattggctggccactccagaccccccgcccactcctc cactcgggtagccggactccccgccccccagcaccgcccggagccccgc -continued
cctcgcctctccctccgcgccccccgcccgcgcgcccagcgggctccgctc ggctcgcgctgcgacccgcccgcgcgctggtcccgcccccggggcgcac ggctctataaatacagctgcgcggcgggccgggcgagagcgtagtggagg

[Transcriptional Start Site]
AGGCGCGGTTGTGAGTAGTACCGGGAGTGGGGTGATCCCGGGCTAGGGGA

GCGCGGCGGCCGCGATCGGGCTTAGTCGGAGCTCCGAAGGGAGTGACTAG

GACACCCGGGTGGGCTACTTTTCTTCCGGTGCTTTTGCTTTTTTTTCCT

TTGGGCTCGGGCTGAGTGTCGCCCACTGAGCAAAGATTCCCTCGTAAAAC

CCAGAGCGACCCTCCCGTCAATTGTTGGGCTCGGGAGTGTCGCGGTGCCC

CGAGCGCGCCGGGCGCGGAGGCAAAGGGAGCGGAGCCGGCCGCGGACGGG

GCCCGGAGCTTGCCTGCCTCCCTCGCTCGCCCCAGCGGGTTCGCTCGCGT

AGAGCGCAGGGCGCGCGCGATGAAGGCGGTGAGCCCGGTGCGCCCCTCGG

GCCGCAAGGCGCCGTCGGGCTGCGGCGGCGGGGAGCTGGCGCTGCGCTGC

CTGGCCGAGCACGGCCACAGCCTGGGTGGCTCCGCAGCCGCGGCGGCGGC

A "promoter" is a region of DNA extending 150-300 bp upstream from the transcription start site that contains binding sites for RNA polymerase and a number of proteins that regulate the rate of transcription of the adjacent gene. The promoter region of the ID4 gene is known in the art. For example, the minimal promoter region of human ID4 is located at −48-+32 (FIG. 1).

Methods for extracting DNA from biological samples and determining the methylation level of a gene promoter are well known in the art. Commonly, DNA isolation procedures comprise lysis of cells using detergents. After cell lysis, proteins are removed from DNA using various proteases. DNA is then extracted with phenol, precipitated in alcohol, and dissolved in an aqueous solution.

The methylation level of a gene promoter can be determined, for example, by methylation-specific PCR, bisulfite sequencing (COBRA), pyrosequencing, or methylation-sensitive restriction enzymes.

More specifically, a method for determining the methylation state of nucleic acids is described in U.S. Pat. No. 6,017,704, which is incorporated herein in its entirety. Methylation-specific PCR (ASP) is a technique whereby DNA is amplified by PCR dependent upon the methylation state of the DNA. Determining the methylation state of a nucleic acid includes amplifying the nucleic acid by means of oligonucleotide primers that distinguishes between methylated and unmethylated nucleic acids. MSP can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracil, and subsequent amplification with primers specific for methylated versus unmethylated DNA. MSP requires only small quantities of DNA, is sensitive to 0.1% methylated alleles of a given CpG island locus, and can be performed on DNA extracted from paraffin-embedded samples. MSP eliminates the false positive results inherent to previous PCR-based approaches which relied on differential restriction enzyme cleavage to distinguish methylated from unmethylated DNA. This method is very simple and can be used on small amounts of tissue or few cells and fresh, frozen, or paraffin-embedded sections. MSP product can be detected by gel electrophoresis, capillary array electrophoresis, or real-time quantitative PCR.

Bisulfite sequencing is widely used to detect 5-methylcytosine (5-MeC) in DNA. It provides a reliable way of detecting any methylated cytosine at single-molecule resolution in any sequence context. The process of bisulfite treatment exploits the different sensitivity of cytosine and 5-MeC to deamination by bisulfite under acidic conditions, in which cytosine undergoes conversion to uracil while 5-MeC remains unreactive. Assessment of the paraffin-embedded specimen can be performed directly on a tissue section (5-12 microns thick) on the slide using bisulfite modification following extraction of DNA and MSP analysis.

Gene expression can be detected and quantified at mRNA or protein level using a number of means well known in the art. To measure mRNA levels, cells in biological samples (e.g., cultured cells, tissues, and body fluids) can be lysed and the mRNA levels in the lysates or in RNA purified or semi-purified from the lysates determined by any of a variety of methods familiar to those in the art. Such methods include, without limitation, hybridization assays using detectably labeled gene-specific DNA or RNA probes and quantitative or semi-quantitative RT-PCR (e.g., real-time PCR) methodologies using appropriate gene-specific oligonucleotide primers. Alternatively, quantitative or semi-quantitative in situ hybridization assays can be carried out using, for example, unlysed tissues or cell suspensions, and detectably (e.g., fluorescently or enzyme-) labeled DNA or RNA probes. Additional methods for quantifying mRNA levels include RNA protection assay (RPA), cDNA and oligonucleotide microarrays, and colorimetric probe based assays.

Methods of measuring protein levels in biological samples are also known in the art. Many such methods employ antibodies (e.g., monoclonal or polyclonal antibodies) that bind specifically to target proteins. In such assays, an antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of test cells, and others (e.g., immunohistological methods or fluorescence flow cytometry) applied to unlysed tissues or cell suspensions. Methods of measuring the amount of a label depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The invention further provides methods for pancreatic cancer diagnosis and prognosis. One method is used to determine whether a subject is suffering from or at risk for developing pancreatic cancer. In this method, a biological sample is obtained from a subject, and the methylation level of an ID4 gene promoter or the expression level of an ID4 gene in the sample is determined. If the methylation level of the ID4 gene promoter in the sample is higher than a control methylation level or the expression level of the ID4 gene in the sample is lower than a control expression level, the subject is likely to be suffering from or at risk for developing pancreatic cancer, e.g., primary or metastatic pancreatic cancer. The control methylation level of the ID4 gene promoter and the control expression level of the ID4 gene may be, for example, the methylation level and the expression level detected in a biological sample from a normal subject or a normal biological sample from the test subject.

In another method, a pancreatic cancer cell is provided, and the methylation level of an ID4 gene promoter or the expression level of an ID4 gene in the cell is determined as described above. The angiogenesis or chemotaxis of the cell is then analyzed. If the methylation level of the ID4 gene promoter in the cell is higher than a control methylation level or the expression level of the ID4 gene in the cell is lower than a control expression level, it indicates an increase in the angiogenesis or chemotaxis of the cell.

The angiogenesis of a cell may be analyzed using any of the methods known in the art. For example, in vivo or model system may be analyzed by induction of blood vessels, induction of angiogenesis growth factors (VEGF), and chick embryo chorioallantoic membrane (CAM assay.

Methods for analyzing the chemotaxis of a cell are also known in the art. Such methods include in vitro cell migration or invasive assay using Boyden Chambers and cell culture wound healing assay.

In addition, the invention provides a method for screening drugs for treating pancreatic cancer. The method involves the steps of providing a pancreatic cancer cell that contains an ID4 gene promoter or expresses an ID4 gene, contacting the cell with a test compound, and determining the methylation level of the ID4 gene promoter or the expression level of the ID4 gene in the cell. If the methylation level of the ID4 gene promoter in the cell is lower than a control methylation level or the expression level of the ID4 gene in the cell is higher than a control expression level, the test compound is identified as a candidate for treating pancreatic cancer. The control methylation level and the control expression level may be, for example, the methylation level and the expression level detected in the pancreatic cancer cell prior to the contacting step. The method may optionally include a step of manufacturing the identified candidate compound.

The test compounds of the present invention can be obtained using any of the numerous approaches (e.g., combinatorial library methods) known in the art. See, e.g., U.S. Pat. No. 6,462,187. Such libraries include, without limitation, peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, and the "one-bead one-compound" libraries. Compounds in the last three libraries can be peptides, non-peptide oligomers, or small molecules. Examples of methods for synthesizing molecular libraries can be found in the art. Libraries of compounds may be presented in solution, or on beads, chips, bacteria, spores, plasmids, or phages.

To identify a compound for treating pancreatic cancer, a pancreatic cancer cell or a subject suffering from pancreatic cancer is provided. The cell or the subject contains an ID4 gene promoter or expresses an ID4 gene. It may be a cell or subject that naturally contains an ID4 gene promoter or expresses an ID4 gene, or alternatively, a cell or subject that contains a recombinant form of an ID4 gene promoter or expresses a recombinant form of an ID4 gene.

The information obtained from the diagnostic and prognostic methods and the screening assays may be used for optimizing the design of a compound for treating pancreatic cancer, manufacturing a candidate compound identified using the screening assays, or treating pancreatic cancer with appropriate compounds.

The compounds of the invention can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration. Other active compounds can also be incorporated into the compositions.

A pharmaceutical composition is often formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated; each unit containing a predetermined quantity of active compound calculated to produce the desired therapeutic effect in association with the required pharmaceutical carrier.

Moreover, the invention provides a method of inhibiting the methylation of an ID4 gene promoter or enhancing the expression of an ID4 gene in a cell in vivo and in vitro. The method involves the steps of providing a pancreatic cancer cell, and contacting the cell with a compound that decreases the methylation level of an ID4 gene promoter or increases the expression level of an ID4 gene in the cell.

For example, the compound may be an ID4 protein or a nucleic acid encoding an ID4 protein. Additionally, the compound may be an agent that activates an ID4 gene, including transcription factor proteins, serum growth factors, tissue inhibitor of matrix metalloproteinase-1 (TIMP-1), and YY1 (a lineage-specific repressor of transcriptional inhibitors).

The therapeutic compound can be a demethylating agent such as 5-aza-cytidine or a compound capable of demethylating CpG islands methylated in promoter regions. These compounds can reverse gene silencing and activate gene expression. Other types of compounds are histone deacetylase (HDAC) inhibitors such as Trichostatin which can modify histones in chromatin regions and activate genes silenced by methylation of CpG islands in promoter regions. There are HDAC inhibitors available for in vitro and clinical trials.

The invention also provides a method for treating pancreatic cancer. The method involves the steps of identifying a subject suffering from or at risk for developing pancreatic cancer, and administering to the subject an effective amount of a compound that decreases the methylation level of the ID4 gene promoter or increases the expression level of the ID4 gene in the subject. A subject to be treated may be identified in the judgment of the subject or a health care professional, and can be subjective (e.g., opinion) or objective (e.g., measurable by a test or diagnostic method such as those described above).

The term "treating" is defined as administration of a substance to a subject with the purpose to cure, alleviate, relieve, remedy, prevent, or ameliorate a disorder, symptoms of the disorder, a disease state secondary to the disorder, or predisposition toward the disorder. A subject to be treated may be identified, e.g., using the diagnostic method described above.

An "effective amount" is an amount of a compound that is capable of producing a medically desirable result in a treated subject. The medically desirable result may be objective (i.e., measurable by some test or marker) or subjective (i.e., subject gives an indication of or feels an effect). The treatment methods can be performed alone or in conjunction with other drugs and/or radiotherapy. See, e.g., U.S. Patent Application 20040224363.

In one in vivo approach, a therapeutic compound (e.g., a compound that decreases the methylation level of an ID4 gene promoter or increases the expression level of an ID4 gene in a subject) itself is administered to a subject.

Generally, the compound will be suspended in a pharmaceutically-acceptable carrier and administered orally or by intravenous (i.v.) infusion, or injected or implanted subcutaneously, intramuscularly, intrathecally, intraperitoneally, intrarectally, intravaginally, intranasally, intragastrically, intratracheally, or intrapulmonarily. For treatment of cancer, the compound is preferably delivered directly to tumor cells, e.g., to a tumor or a tumor bed following surgical excision of the tumor, in order to kill any remaining tumor cells. For prevention of cancer invasion and metastases, the compound can be administered to, for example, a subject that has not yet developed detectable invasion and metastases but is found to have an increased methylation level of an ID4 gene promoter or a decreased expression level of an ID4 gene. The dosage required depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by i.v. injection.

Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

In some embodiments, polynucleotides are administered to a subject. Polynucleotides can be delivered to target cells by, for example, the use of polymeric, biodegradable microparticle or microcapsule devices known in the art. Another way to achieve uptake of the nucleic acid is using liposomes, prepared by standard methods. The polynucleotides can be incorporated alone into these delivery vehicles or co-incorporated with tissue-specific or tumor-specific antibodies. Alternatively, one can prepare a molecular conjugate composed of a polynucleotide attached to poly-L-lysine by electrostatic or covalent forces. Poly-L-lysine binds to a ligand that can bind to a receptor on target cells. "Naked DNA" (i.e., without a delivery vehicle) can also be delivered to an intramuscular, intradermal, or subcutaneous site. A preferred dosage for administration of polynucleotide is from approximately $10^6$ to $10^{12}$ copies of the polynucleotide molecule.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE

DNA Methylation of Transcription Factor ID4 Regulates Chemotaxis and Angiogenesis of Pancreatic Cancer Introduction Epigenetic modifications of transcription factor ID4, a helix-loop-helix inhibitory transcription factor, appear to promote cancer progression. Pancreatic cancer is often characterized by epigenetic modifications of tumor suppressor genes. It was believed that loss of ID4 expression may have a role in the progression of pancreatic cancer, and that ID4 regulates the growth and invasion of pancreatic cancer.

Methods

Established pancreatic cancer cell lines were screened for ID4 expression by a quantitative real-time RT-PCR (qRT) assay. In cell lines with absent ID4 expression, epigenetic modifications of the ID4 promoter region CpG islands were assessed to determine the role of DNA hypermethylation as the cause of absent ID4 expression. A short-interfering RNA (siRNA) assay for ID4 was developed to assess the specific contributions of ID4 gene expression to pancreatic cancer cell proliferation, chemotaxis, and angiogenesis. Abrogation of ID4 expression in pancreatic cancer cells lines by an siRNA assay was measured by qRT and immunohistochemistry (IHC). Tumor specimens from patients with pancreatic ductal adenocarcinoma (PDAC) were assessed for DNA hypermethylation of ID4.

Pancreatic cancer lines assessed included PANC1, Mia-PACA2, CAPAN1, Hs766T, BxPC3, COLO357, AsPC1, and CFPAC-1. DNA from cell lines was extracted using DNAzol. DNA from paraffin-embedded specimens was extracted using a Qiagen kit. DNA was modified with sodium bisulfite to assess methylation of specific CpG islands in the promoter region of ID4. Methylation specific PCR was performed for ID4 DNA with primers for methylated/unmethylated ID4. The methylation status of ID4 was determined by CEQ analysis (Beckman Coulter).

Results

Cell Lines

Figure 2:
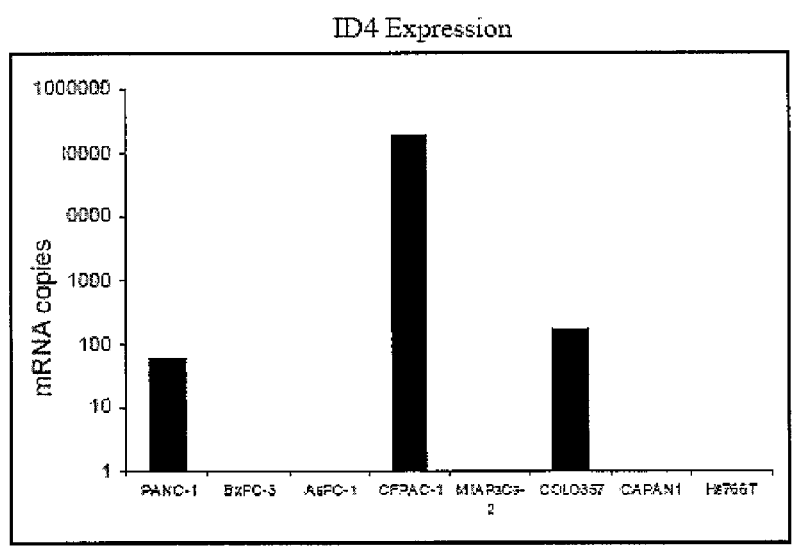
FIG. 2. ID4 expression in pancreatic cancer cell lines.

Screening of eight pancreatic cancer cell lines (AsPC-1, MIA PaCa-2, PANC-1, CAPAN-1, Hs766T, CFPAC-1, BxPC-3, and COLO357) for ID4 expression by qRT demonstrated that 5 of 8 (62%) cell lines showed no ID4 expression (FIG. 2). Cell lines with absent ID4 expression were assessed for hypermethylation of the ID4 DNA promoter region. Methylation specific PCR demonstrated complete methylation of the CpG islands of the ID4 promoter region in these cell lines.

Clinical Specimens

Specimens from 20 patients who underwent curative resection for pancreatic cancer were accrued. Analysis of 20 PDAC (pancreatic ductal adenocarcinoma) specimens demonstrated complete methylation of the ID4 promoter region CpG islands in primary tumors in 17 of 20 (85%) patients.

Figure 3:
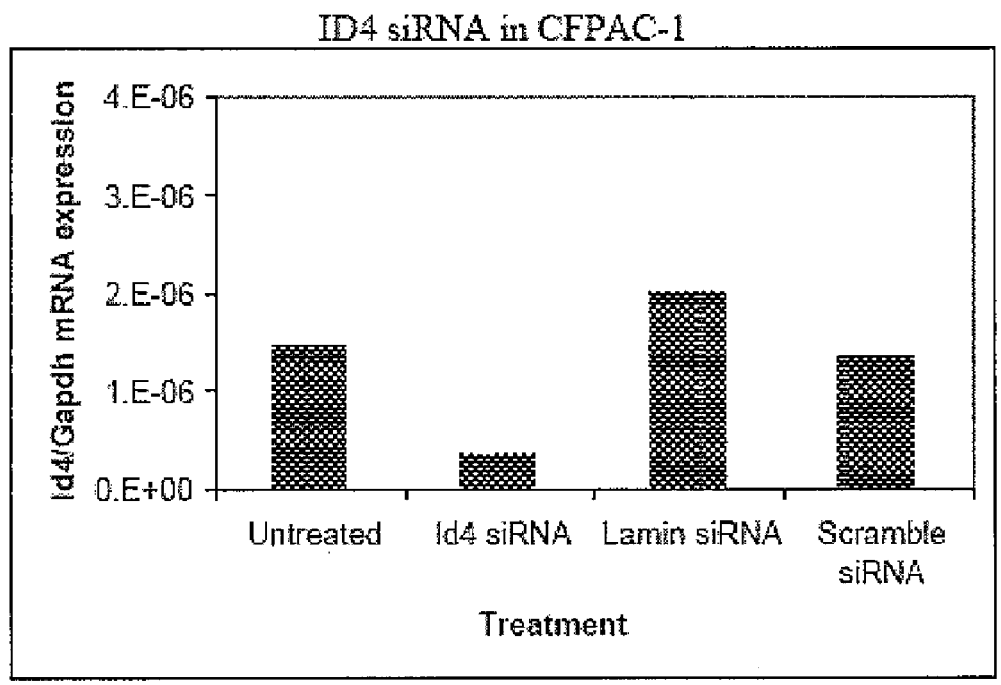
FIG. 3. ID4 siRNA in CFPAC-1.
Figure 4:
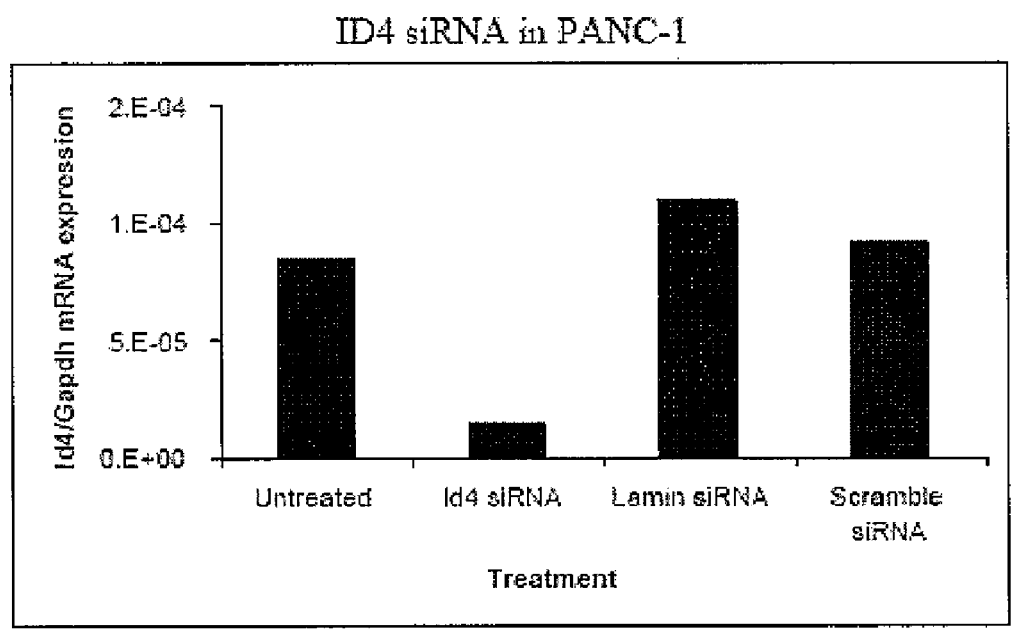
FIG. 4. ID4 siRNA in PANC-1.
Figure 5:
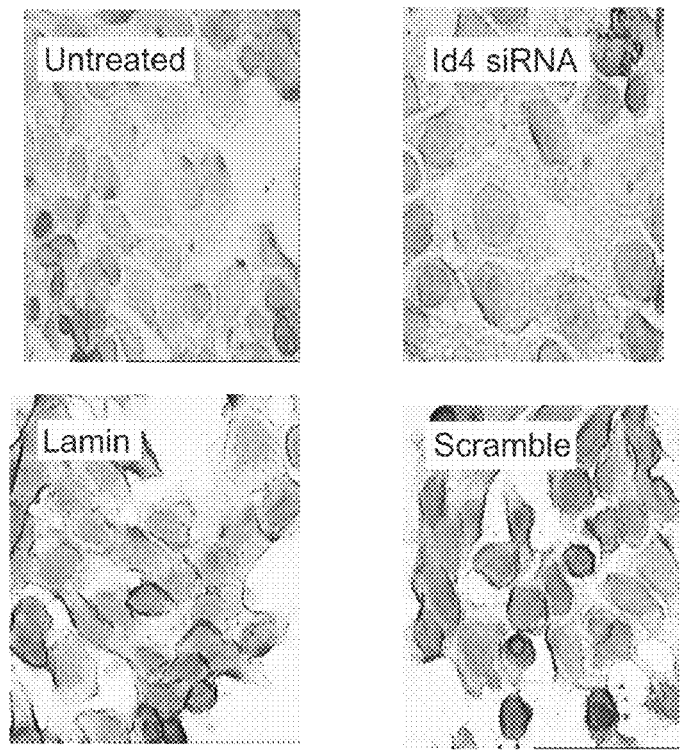
FIG. 5. IHC for ID4 siRNA-CFPAC-1.

Short Interfering RNA (siRNA) Assay siRNA transfection was performed with Lipofectamine2000. Positive (Lamin) and negative (nonsense) siRNA controls were included. Transfection efficiency was assessed by qRT and IHC. The efficiency of siRNA knockout on ID4 expression measured by qRT showed 80%-90% decrease in ID4 expression with siRNA. This result was corroborated by IHC. See FIGS. 3-5.

Cell Viability

Figure 6:
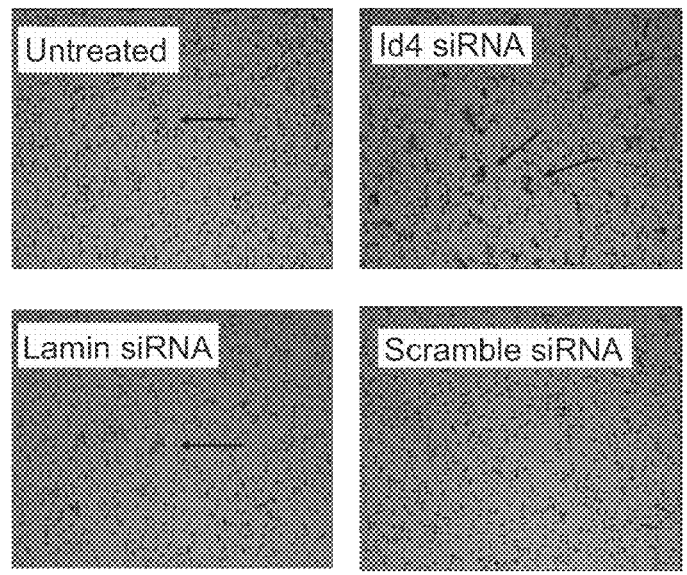
FIG. 6. Migration Assay—CFPAC-1.
Figure 7:
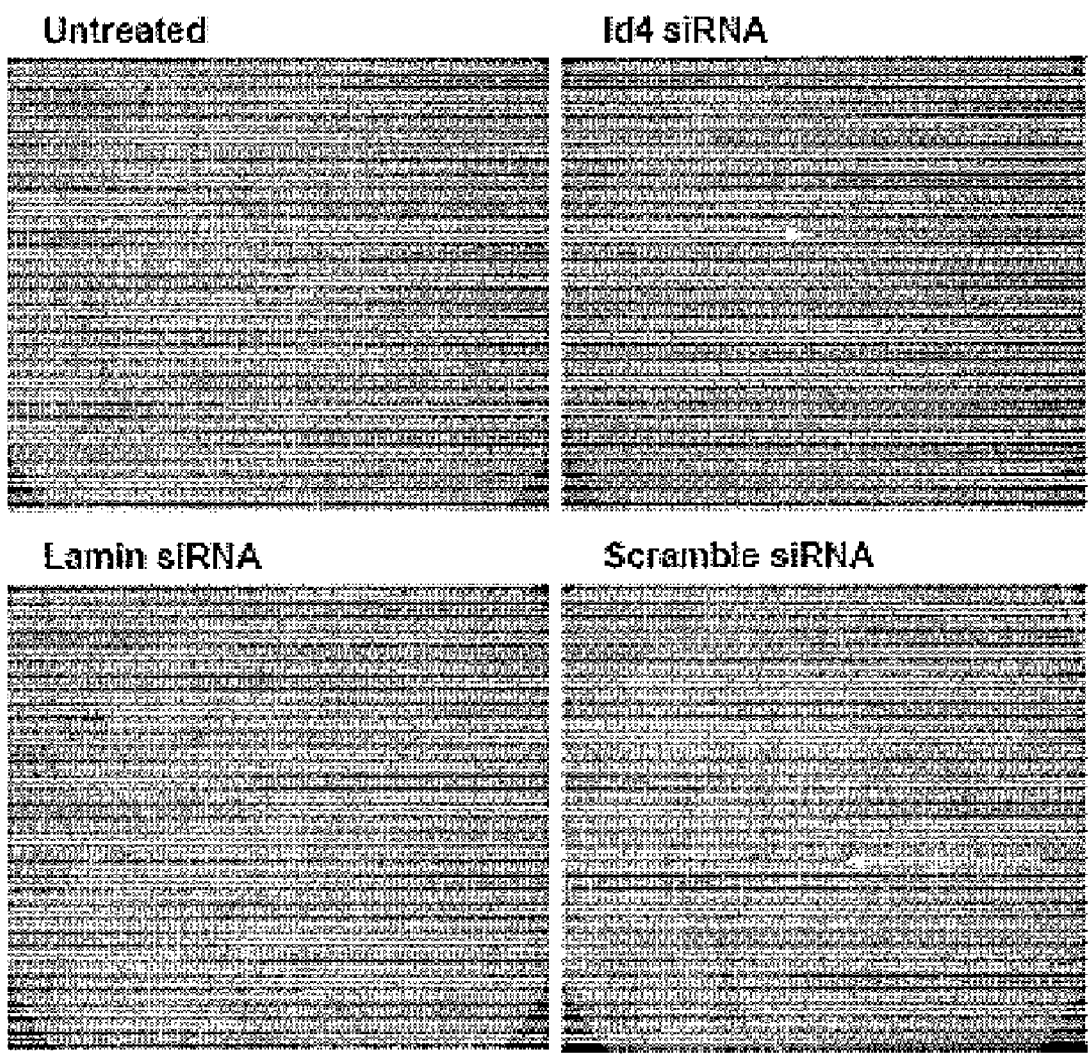
FIG. 7. Angiogenesis Assay—CFPAC-1.

Cells were assessed after transfection with ID4 siRNA. Trypan blue exclusion test was performed. Abrogation of ID4 expression in pancreatic cancer cells resulted in an increase in endothelial cell angiogenesis by an in vitro assay. Similarly, there was an increase in cancer cell chemotaxis with a decrease in ID4 expression. However, there was no significant change in proliferation with ID4 siRNA. See FIGS. 6-7.

CONCLUSIONS

ID4 undergoes epigenetic silencing. It promotes growth and abrogates migration. Expression of transcription factor ID4 appears to result in the inhibition of pancreatic cancer cell chemotaxis and endothelial cell angiogenesis, verifying its endogenous inhibitory role. ID4 expression appears to be regulated by DNA promoter region CpG island hypermethylation, which is a frequent clinical finding. This study identifies a transcription factor that suppresses pancreatic cancer progression. Potential future treatment strategies should favor recapitulation of ID4 expression.

DISCUSSION

ID4 is frequently silenced in pancreatic cancer, which may enhance the migratory/invasive phenotype of pancreatic cancer. Recapitulation of ID4 expression in human pancreatic cancer may preferentially limit migration/invasion of pancreatic cancer.

All publications cited herein are incorporated by reference in their entirety.

What is claimed is:

1. A method of determining whether a human subject is suffering from or at risk for developing pancreatic cancer, comprising:
    obtaining a pancreatic tumor tissue sample from the human subject;
    measuring a methylation level of an ID4 (inhibitor of DNA binding 4) gene promoter or an expression level of an ID4 gene; and
    determining that the human subject is likely to be suffering from or at risk for developing pancreatic cancer when the methylation level of the ID4 gene promoter is higher than a control methylation level or the expression level of an ID4 gene in the sample is lower than a control expression level.

2. The method of claim 1, wherein the pancreatic cancer is primary or metastatic pancreatic cancer.

3. The method of claim 1, wherein the methylation level of the ID4 gene promoter is determined by quantitative methylation-specific polymerase chain reaction (MSP) or bisulfite sequencing.

4. The method of claim 1, wherein the expression level of the ID4 gene is determined at an mRNA level or a protein level.

5. The method of claim 4, wherein the expression level of the ID4 gene is determined by quantitative polymerase chain reaction (PCR) or immunohistochemistry (IHC).

6. The method of claim 1, wherein the pancreatic tumor tissue sample is a primary pancreatic tumor tissue sample or a metastatic tumor tissue sample.

7. The method of claim 1, wherein the pancreatic tumor tissue sample is a normal or benign tumor tissue sample.

8. The method of claim 1, wherein the pancreatic tumor tissue sample is selected from the group consisting of a freshly prepared tumor tissue sample, a frozen tumor tissue sample and a paraffin-embedded tumor tissue sample.

9. A method for diagnosing a migratory or invasive phenotype of a pancreatic tumor in a human subject, comprising:
    obtaining a pancreatic tumor tissue sample from the human subject;
    measuring a methylation level of an ID4 (inhibitor of DNA binding 4) gene promoter or an expression level of an ID4 gene; and
    determining that the pancreatic tumor is likely to be migratory or invasive when the methylation level of the ID4 gene promoter is higher than a control methylation level or the expression level of an ID4 gene in the sample is lower than a control expression level.

10. The method of claim 9, wherein the pancreatic tumor tissue sample is a primary pancreatic tumor tissue sample or a metastatic tumor tissue sample.

11. The method of claim 9, wherein the pancreatic tumor tissue sample is a normal or benign tumor tissue sample.

12. The method of claim 9, wherein the pancreatic tumor tissue sample is selected from the group consisting of a freshly prepared tumor tissue sample, a frozen tumor tissue sample and a paraffin-embedded tumor tissue sample.

13. The method of claim 9, wherein the methylation level of the ID4 gene promoter is determined by quantitative methylation-specific polymerase chain reaction (MSP) or bisulfite sequencing.

14. The method of claim 9, wherein the expression level of the ID4 gene is determined at an mRNA level or a protein level.

15. The method of claim 14, wherein the expression level of the ID4 gene is determined by quantitative polymerase chain reaction (PCR), flow cytometry or immunohistochemistry (IHC).

16. The method of claim 9 wherein a diagnosis of a migratory or invasive phenotype indicates that the pancreatic tumor has likely metastasized or will likely metastasize.

17. A method for determining a migratory or invasive pancreatic cancer cell phenotype, comprising:
    obtaining a pancreatic cancer cell from a pancreatic cell culture or a pancreatic tumor tissue from a subject having pancreatic cancer;
    measuring a methylation level of an ID4 (inhibitor of DNA binding 4) gene promoter or an expression level of an ID4 gene; and
    determining that the pancreatic cancer cell is likely to be migratory or invasive when the methylation level of the ID4 gene promoter is higher than a control methylation level or the expression level of an ID4 gene in the sample is lower than a control expression level.

18. The method of claim 9, further comprising analyzing the pancreatic cell's effects on chemotaxis and/or angiogenesis; and
    determining that the pancreatic cancer cell is likely to be migratory or invasive when the pancreatic cancer cell shows an effect of increased chemotaxis and/or angiogenesis.

19. The method of claim 17 wherein the expression level of the ID4 gene is determined at an mRNA level or a protein level.

20. The method of claim 17 wherein when the determination of a migratory or invasive cellular phenotype indicates that the pancreatic cancer cell has likely metastasized or will likely metastasize.

* * * * *